United States Patent [19]

Oka et al.

[11] Patent Number: 5,349,093
[45] Date of Patent: Sep. 20, 1994

[54] FLUOROVINYL ETHER

[75] Inventors: Masahiko Oka, Ohtsu; Mitsuru Kishine; Hideya Saito, both of Osaka; Masuo Kokumai, Hyogo, all of Japan

[73] Assignee: Daikin Industries, Ltd., Osaka, Japan

[21] Appl. No.: 31,024

[22] Filed: Mar. 11, 1993

Related U.S. Application Data

[63] Continuation of Ser. No. 879,454, May 4, 1992, abandoned, which is a continuation of Ser. No. 600,248, Oct. 22, 1990, abandoned, which is a continuation of Ser. No. 465,609, Jan. 18, 1990, abandoned, which is a continuation of Ser. No. 185,916, Apr. 25, 1988, abandoned.

Foreign Application Priority Data

Apr. 25, 1987 [JP] Japan ................. 62-102930

[51] Int. Cl.$^5$ .............................................. C07C 43/14
[52] U.S. Cl. ................................................... 568/615
[58] Field of Search ...................................... 568/615

[56] References Cited

U.S. PATENT DOCUMENTS 3,114,778 12/1963 Fritz et al. ............................. 568/674
4,546,157 10/1985 Nakagawa et al. .
4,556,747 12/1985 Resnick ................................. 568/674

FOREIGN PATENT DOCUMENTS 0077998 5/1983 European Pat. Off. .
0130052 1/1985 European Pat. Off. .
0150618 8/1985 European Pat. Off. .
0158854 10/1985 European Pat. Off. .
0199138 6/1986 European Pat. Off. .
0219065 4/1987 European Pat. Off. .
0260773 3/1988 European Pat. Off. .
1341087 9/1963 France .

OTHER PUBLICATIONS

Sass et al. II, Zh Ong Khim, 1973, 9(2) 225–228.
D'Yachishima et al., J. Org. Chim., USSR 8 (1972) pp. 1790–1793 (Translation pp. 1836–1838).
Sass et al., Vyso-Komol, Saedin. Ser A, 1975, 17(5) 1086–1911.
Erenburg et al., Vysokomol, Saedin Ser A 1979 21(10) 2261–2266.

*Primary Examiner*—Howard T. Mars
*Attorney, Agent, or Firm*—Birch, Stewart Kolasch & Birch

[57] ABSTRACT

A fluorovinyl ether of the formula:

$$R_f-(OCF_2CF_2CF_2)_n-OCF=CF_2 \qquad (I)$$

wherein $R_f$ is a $C_1$–$C_5$ perfluoroalkyl group, n is an integer of 1 to 4 provided that when n is 1 (one), $R_f$ is other than a trifluoromethyl group, a copolymer of which with an ethylenically unsaturated compound has a low glass transition temperature and improved low temperature properties.

2 Claims, No Drawings

FLUOROVINYL ETHER

This application is a application under 37 CFR 1.62 of prior application Ser. No. 07/879,454, filed on May 4, 1992, which is a continuation of Ser. No. 07/600,248, filed on Oct. 22, 1990, which is a continuation of Ser. No. 07/465,609, filed on Jan. 18, 1990, which is a continuation of Ser. No. 07/185,916, filed Apr. 25, 1988, all now abandoned.

BACKGROUND OF THE INVENTION

1. Field of the Invention

The present invention relates to a novel fluorovinyl ether. More particularly, it relates to a fluorovinyl ether which is a useful modifier for a polymer comprising an ethylenically unsaturated compound.

2. Description of the Related Art

Copolymerization of two or more fluoroolefins or a fluoroolefin with a fluorine-free olefin gives various kinds of copolymers from a resin to an elastomer according to a composition of the monomers. The copolymer comprising the fluoroolefin can be molded to produce mechanical parts (e.g. O-rings, flange seals, gaskets, diaphragms, liners, etc.) and particularly useful in cases where special resistances to heat and corrosive fluids are required.

As fluorine-containing elastomers, known are copolymers of vinylidene fluoride/hexafluoropropylene, tetrafluoroethylene/propylene, tetrafluoroethylene/perfluoro-(alkyl vinyl ether), vinylidene fluoride/perfluoro(alkyl vinyl ether) and the like.

These fluorine-containing elastomeric copolymers has insufficient properties at low temperature and are hardly used at low temperature, although they are superior to hydrocarbon type elastomers in heat resistance, oil resistance chemical resistance and so on.

To overcome such drawbacks of the fluorine-containing elastomers, a blending method such as co-cross linking with a silicone rubber has been attempted. However, to improve the low temperature properties, the blend should comprise the silicone rubber as a main component so that the characteristics of the fluorine-containing elastomer are suppressed. Alternatively, addition of a certain kind of plasticizer to the fluorine-containing elastomer is proposed. However, under some conditions, the plasticizer is separated. Therefore, the intended elastomer having good resistance to low temperature has not been provided.

To improve the low temperature properties of the fluorine-containing elastomer by introduction of ether linkages in its backbone chain, ionic polymerization of hexafluoropropylene oxide, radical polymerization of a fluorine-containing ketone and condensation of fluorine-containing polyether are investigated. However, no practical elastomer has been produced by these methods.

Introduction of an ether linkage in a side chain of the fluorine-containing elastomer has been studied to improve the low temperature properties. For example, copolymerization of vinylidene fluoride or tetrafluoroethylene with a fluoro(alkyl vinyl ether) of the formula:

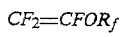

$CF_2=CFOR_f$ wherein $R_f$ is a perfluoroalkyl group such as $-CF_3$, $-C_2F_5$ or $-C_3F_7$ gives an elastomeric copolymer. However, a glass transition temperature ($T_g$) of the copolymer cannot be sufficiently lowered even when a content of the fluoro(alkyl vinyl ether) is increased as high as possible.

Among the fluorovinyl ethers, a fluorovinyl ether having plural ether linkages in a molecule can effectively improve the low temperature properties of the fluorine-containing elastomer. By copolymerizing the fluorovinyl ether having plural ether linkages with the fluorine-free olefin or the fluroolefin, a fluoroelastomer having low temperature properties to some extent is produced (cf. Japanese Patent Kokai Publication No. 18710/1982 and Japanese Patent Publication Nos. 50486/1986 and 57324/1987). However, none of them has satisfactory low temperature properties.

SUMMARY OF THE INVENTION

One object of the present invention is to provide a novel fluorovinyl ether which is copolymerized with a fluoroolefin or a fluorine-free olefin to give a copolymer with good low temperature properties in addition to heat resistance, oil resistance and chemical resistance.

Another object of the present invention is to provide a fluorine-containing elastomeric copolymer having improved low temperature properties.

These and other objects of the present invention are accomplished by a fluorovinyl ether of the formula:

$$R_f-(OCF_2CF_2CF_2)_n-OCF=CF_2 \qquad (I)$$

wherein $R_f$ is a $C_1$—$C_5$ perfluoroalkyl group, n is an integer of 1 to 4 provided that when n is 1 (one), $R_f$ is other than a trifluoromethyl group.

DETAILED DESCRIPTION OF THE INVENTION

Specific examples of the fluorovinyl ether (I) are:

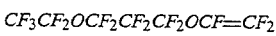
$CF_3CF_2OCF_2CF_2CF_2OCF=CF_2$

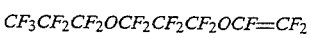
$CF_3CF_2CF_2OCF_2CF_2CF_2OCF=CF_2$

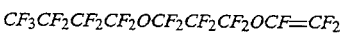
$CF_3CF_2CF_2CF_2OCF_2CF_2CF_2OCF=CF_2$

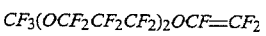
$CF_3(OCF_2CF_2CF_2)_2OCF=CF_2$

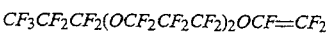
$CF_3CF_2CF_2(OCF_2CF_2CF_2)_2OCF=CF_2$

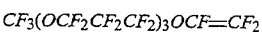
$CF_3(OCF_2CF_2CF_2)_3OCF=CF_2$

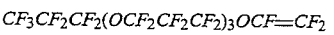
$CF_3CF_2CF_2(OCF_2CF_2CF_2)_3OCF=CF_2$

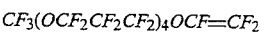
$CF_3(OCF_2CF_2CF_2)_4OCF=CF_2$

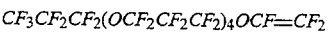
$CF_3CF_2CF_2(OCF_2CF_2CF_2)_4OCF=CF_2$

Among the fluorovinyl ether (I), those in which n is 2, 3 or 4 are preferred.

The fluorovinyl ether (I) may be prepared from a corresponding acid fluoride according to the following reaction scheme:

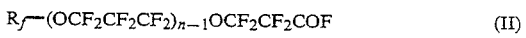
$$R_f-(OCF_2CF_2CF_2)_{n-1}OCF_2CF_2COF \qquad (II)$$

$$\downarrow \begin{array}{l} + \text{ Hexafluoropropylene oxide} \\ \text{(A catalyst and a solvent)} \end{array}$$

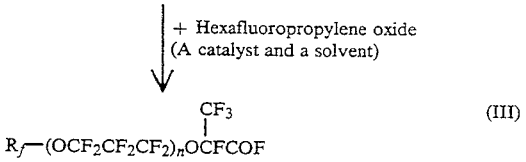
$$R_f-(OCF_2CF_2CF_2)_nOCFCOF \overset{CF_3}{|} \qquad (III)$$

-continued

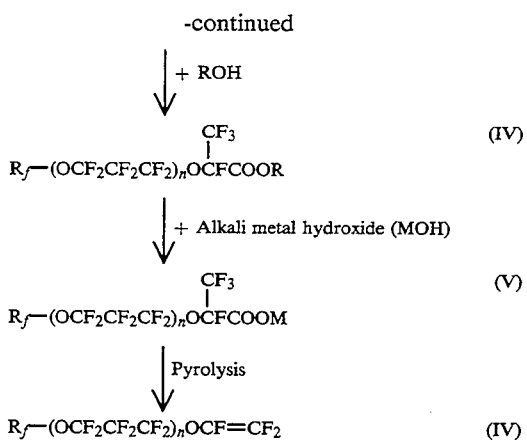

wherein R is an alkyl group or a cycloalkyl or aryl group which may have a substituent and $R_f$ and n are the same as defined above.

The compound (II) can be prepared by the method disclosed in Japanese Patent Kokai Publication No. 113616/1986, U.S. patent application Ser. No. 940,191 and EP-A-0 148 482, the disclosures of which are hereby incorporated by reference.

The compound (III) is prepared by reacting the compound (II) with hexafluoropropylene oxide. Examples of the solvent are glymes such as ethyleneglycol dimethyl ether, diethyleneglycol dimethyl ether and tetraethyleneglycol dimethyl ether and acetonitrile. Examples of the catalyst are cesium fluoride, potassium fluoride, silver fluoride, ammonium fluoride, tetraalkylammonium fluoride, sulfonium fluoride and the like.

The reaction temperature and time are not critical. Typically, the reaction from the compound (II) to the compound (III) is carried out at a temperature of from $-30°$ C. to $+50°$ C. for 3 to 20 hours.

The compound (IV) is prepared by gradually reacting the compound (III) with the alcohol (ROH) while cooling the reaction system with iced water.

The compound (V) is prepared by reacting the compound (IV) with the alkali metal hydroxide such as sodium hydroxide at a temperature of from room temperature to 100° C. for several hours.

By heating the compound (V) under reduced pressure or in an inert gas such as nitrogen at a temperature of from 150° C. to 250° C., the desired compound (I) is produced.

The ethylenically unsaturated compound to be copolymerized with the compound (I) may be any of conventionally known ones. Examples of the fluorine-free ethylenically unsaturated compound are ethylene, propylene, butylene, vinyl esters of carboxylic acids (e.g. vinyl acetate), vinyl ethers (e.g. methyl vinyl ether and ethyl vinyl ether), vinyl chloride, vinylidene chloride, acrylic acid and methacrylic acid. Examples of the fluorine containing ethylenically unsaturated compound are tetrafluoroethylene, trifluoroethylene, chlorotrifluoroethylene, vinyl fluoride, vinylidene fluoride, hexafluoropropylene, pentafluoropropylene, hexafluoroisobutene, perfluorocyclobutene, perftuoro(methylcyclobutene), perfluoroallene, $\alpha,\beta,\beta$-trifluorostyrene, perfluorostyrene, perfluoro(alkyl vinyl ether) (e.g. perfluoro(methyl vinyl ether) and perfluoro(propyl vinyl ether)), perfluoro(alkyl vinyl polyether)s, polyfluoroacrylic acid, polyfluorovinyl acetate, polyfluorovinyl ether sulfonate and polyfluorodienes.

The content of the fluorovinyl ether (I) may vary with the kind of the copolymer to be produced. Preferably, the content of the fluorovinyl ether (I) is from 0.01 to 60 by mole based on the whole amount of the copolymer in view of the properties and cost of the copolymer. To improve the low temperature properties of the copolymer, the copolymer comprises preferably from 1 to 60 % by mole, more preferably from 2 to 50 % by mole of the fluorovinyl ether (I).

The copolymer of the present invention may be prepared by any of the conventional polymerization methods such as bulk, suspension and solution polymerization and emulsion polymerization by using a water-soluble or oil-soluble peroxide in the presence of a perfluoroemulsifier. As the solvent used in the solution or emulsion polymerization, preferred are highly fluorinated solvents such as dichlorodifluoromethane, trichlorofluoromethane, chlorodifluoromethane, 1,1,2-dichloro-1,2,2-trifluoroethane, 1,2-dichloro-1,1,2,2-tetrafluoroethane, 1,1,2,2-tetrachloro-1,2-difluoroethane, perfluorocyclobutane, perfluorodimethylcyclobutane and the like.

In the bulk, suspension and solution polymerization, an organic polymerization initiator may be used. Among the initiator, preferred are highly fluorinated organic peroxides. Most preferred is a diacylperoxide of the formula:

$$(R_f{'}-COO-)_2$$

wherein $R_f{'}$ is a perfluoroalkyl group, an $\omega$-hydroperfluoroalkyl group or a perchlorofluoroalkyl group.

The copolymer of the present invention has a number average molecular weight of from 10,000 to 500,000, preferably from 30,000 to 300,000.

The molecular weight of the copolymer can be controlled by the addition of a chain transfer agent. Specific examples of the chain transfer agent are hydrocarbons having 4 to 6 carbon atoms, alcohols, ethers, organic halides (e.g. $CCl_4$, $CBrCl_3$, $CF_2BrCFBrCF_3$ and $CF_2I_2$). When a fluorocarbon iodide such as $CF_2I_2$, $I(CF_2)I$ or $CF_2=CFCF_2CF_2I$ is used as the chain transfer agent, since the iodine atom bonded to the chain terminal is still active, the copolymer can be cross linked with a peroxide as a radical source in the presence of a polyfunctional unsaturated compound such as triallylisocyanurate and triallylcyanurate.

The polymerization temperature depends on a decomposition temperature of the polymerization initiator. The polymerization pressure depends on the kinds of the fluorovinyl ether (I) and the comonomer to be copolymerized and determined from the reaction rate ratio of the fluorovinyl ether (I) to the comonomer so that the content of the fluorovinyl ether (I) falls within the above range.

The cross linking method of the copolymer of the present invention is selected according to the kind of the comonomer. For example, when the comonomer is vinylidene fluoride, trifluoroethylene and/or vinyl fluoride, the copolymer can be cross linked with a polyamine or a combination of an aromatic polyol and a cross linking accelerator. When the comonomer is tetrafluoroethylene, chlorotrifluoroethylene and/or ethylene, the above cross linking method is hardly or not effective and therefore, the copolymer should contain a comonomer which can provide a cross linking site to the copolymer. Examples of the comonomer which provides a cross linking site to the copolymer are $CF_2=CFO(CF_2)_mCN$, 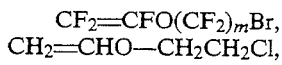
$CF_2=CFO(CF_2)_mI$, $CH_2=CHO—CH_2CH_2Cl$,
$CF_2=CFCF_2COOH$,

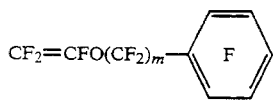

wherein m is an integer of 1 to 8. When the fluorocarbon iodide is used as a chain transfer agent as described above, the copolymer which is easily cross linked with the peroxide is obtained.

The amount of the organic peroxide to be used is from 0.05 to 10 parts by weight, preferably from 1.0 to 5 parts by weight based on 100 parts by weight of the copolymer.

The organic peroxide is generally a peroxide which generates a peroxy radical by heating or in the presence of a redox system. Examples of such peroxide are 1,1-bis(tert.-butylperoxy) -3,5,5-trimethylcyclohexane, 2,5-dimethylhexane -2,5-dihydroperoxide, di-tert.-butylperoxide, tert.-butylcumylperoxide, dicumylperoxide, α,α'-bis(tert.-butylperoxy) -p-diisopropylbenzene, 2,5-dimethyl-2,5-di-(tert.-butylperoxy) hexane, 2,5-dimethyl-2,5-di(tert.-butylperoxy) hexyne-3, benzoylperoxide, tert.-butylperoxybenzene, 2,5-dimethyl-2,5-di(benzoylperoxy)hexane, tert.-butyl peroxymaleate, tert.-butylperoxyisopropyl carbonate and the like. Among them, the dialkyl type peroxides are preferred. The kind and amount of the peroxide depend on an amount of active —O—O— groups, a decomposition temperature and so on.

When the organic peroxide is used for cross linking of the copolymer, co-use of a crosslinking aid or cocross linking agent will promote the curing of the copolymer. Any of the cross linking aid or co-cross linking agent which has a reaction activity with both the peroxy radical and the polymer radical can be used. Preferred examples of the cross linking aid or co-cross linking agent are triallyl cyanurate, triallyl isocyanurate, triacryl formal, triallyl trimellitate, N,N'-m-phenylenebismaleimide, dipropargyl terephthalate, diallyl phthalate, tetraallyl terephthalate, triallyl phosphate and the like. The amount of the cross linking aid or co-cross linking agent is from 0.1 to 10 parts by weight, preferably from 0.5 to 5 parts by weight based on 100 parts by weight of the copolymer.

The copolymer of the present invention can be blended with other polymer and cross linked. Examples of other polymer to be blended are silicone oil and rubber, ethylene/vinyl acetate copolymer, polybutadiene-1,2, fluorosilicone oil and rubber, fluorophosphazene rubber, vinylidene fluoride/hexafluoropropylene copolymer, vinylidene fluoride/tetrafluoroethylene/hexafluoropropylene copolymer, hexafluoropropylene/ethylene copolymer, tetrafluoroethylene/propylene copolymer and other polymers having a radical reactivity. The amount of other polymer to be blended is not critical. However, other polymer is not blended with the copolymer of the present invention in such amount that the inherent properties of the latter are deteriorated.

The copolymer of the present invention may contain any conventional additive such as a pigment for coloring the copolymer, a filler and a reinforcing material. Specific examples of the generally used filler and/or reinforcing material are inorganic materials such as carbon black, $TiO_2$, $SiO_2$, clay and talc and organic materials such as fluoropolymers (e.g. polytetrafluoroethylene, polyvinylidene fluoride, polyvinyl fluoride, polychlorotrifluoroethylene, tetrafluoroethylene/ethylene copolymer, tetrafluoroethylene/vinylidene fluoride copolymer, etc.).

The cross linking component(s) may be compounded with the copolymer of the present invention by a suitable method according to viscoelasticity and form of the materials. When the copolymer and other materials are solid, they are mixed with an open roll, a powder mixer and the like. When they are liquid, a conventional mixer is used for mixing them. Alternatively, the solid materials can be dissolved or dispersed in a suitable medium and then mixed.

The cross linking temperature and time depend on the kind of the peroxide to be used. Usually, press cure is carried out at a temperature of from 120° C. to 200° C. for 5 to 30 minutes and oven cure is carried out at a temperature of from 150° C. to 250° C. for 1 to 24 hours.

The copolymer of the present invention may be used as a molding material, a sealant, an adhesive and a coating material when not only heat resistance, oil resistance, chemical resistance and solvent resistance but also resistance to low temperature are required.

PREFERRED EMBODIMENTS OF THE INVENTION

The present invention will be illustrated by following Examples, in which "%" and "parts" are by weight unless otherwise indicated.

PREPARATION EXAMPLE 1

Preparation of 2,2,5,5,6,6,9,9,10,10,13,13,14, 14,15-pentadecafluro-4,8,12-trioxa-pentadecanoyl fluoride [$FCH_2CF_2CF_2—(OCH_2CF_2CF_2)_2—OCH_2CF_2COF$]

In a 5 liter flask equipped with a stirrer, a condenser and a dropping funnel, 2,2,3-trifluoropropionyl fluoride (1,059 g), crown ether (5 g), cesium fluoride (40 g) and monoglyme (1,000 g) were charged and then 2,2,3,3-tetrafluorooxetane (hereinafter referred to as "tetrafluorooxetane") (1,515 g) was dropwise added over 3.5 hours while stirring at a temperature of from 15° to 20° C. After the addition of tetrafluorooxetane, the mixture was stirred for 5 hours at a temperature of 15° to 20° C. Thereafter, the reaction mixture was distilled under reduced pressure to recover the entitled compound (326 g) at 123° C./5 mmHg.

PREPARATION EXAMPLE 2

In a 100 ml stainless steel made reactor equipped with a condenser, the fluoride prepared in Preparation Example 1 (160 g) was charged. Then, a mixed gas of fluorine and nitrogen (volume ratio of 20:80) was bubbled in the fluoride at a flow rate of 150 ml/min. at 100° C. for 97 hours to obtain a reaction product containing $CF_3CF_2CF_2—(OCF_2CF_2CF_2—CF_2)_2—OCF_2CF_2COF$ (85% by mole) and $CF_3CF_2CF_2—(OCF_2CF_2CF_2)_2—OCF_2CF_3$ (15 % by mole).

PREPARATION EXAMPLE 3

In the same manner as in Preparation Example 2 but using 180 g of the fluoride prepared in Preparation Example 1 and bubbling the mixed gas for 120 hours, the reaction was effected to obtain a reaction product (205 g) containing $CF_3CF_2CF_2—(OCF_2CF_2CF_2$ )$_2$—OCF$_2$CF$_2$COF (95% by mole) and CF$_3$—CF$_2$CF$_2$—(OCF$_2$CF$_2$CF$_2$)$_2$—OCF$_2$CF$_3$(5% by mole).

PREPARATION EXAMPLE 4

In the same manner as in Preparation Example 2 but using 200 g of the fluoride prepared in Preparation Example 1 and bubbling the mixed gas for 96 hours, the reaction was effected to obtain a reaction product (240 g) containing CF$_3$CF$_2$CF$_2$—(OCF$_2$CF$_2$CF$_2$)$_2$—OCF$_2$CF$_2$COF (92% by mole) and CF$_3$—CF$_2$CF$_2$—(OCF$_2$CF$_2$CF$_2$)$_2$—OCF$_2$CF$_3$ (8% by mole).

EXAMPLE 1

Preparation of perfluro(3,7,11,15-tetraoxa-1-octadecene) [CF$_3$CF$_2$CF$_2$—(OCF$_2$CF$_2$CF$_2$)$_3$—$_{OCF=CF2}$]

A) In a one liter four-necked flask containing cesium fluoride (13.3 g) and tetraglyme (27 ml), a mixture of CF$_3$CF$_2$CF$_2$—(OCF CF$_2$CF$_2$)$_2$—OCF$_2$CF$_2$COF (85% by mole) and CF$_3$CF$_2$CF$_2$—(OCF$_2$CF$_2$CF$_2$)$_2$—OCF$_2$CF$_3$ (15% by mole) (234 g) was charged. Then, hexafluoropropylene oxide was flowed in the mixture at such rate that the mixture was refluxed by a dry ice-cooled condenser while stirring with keeping an interior temperature at +10° C. After 3.5 hours from the start of reaction, the flow of hexafluoropropylene oxide was terminated. Then, methanol (30 ml) was added to the reaction mixture while cooling with iced water followed by washing with water several times. The reaction product was distilled to recover a methyl ester of the formula: CF$_3$CF$_2$CF$_2$—(OCF$_2$CF$_2$—CF$_2$)$_3$—OCF(CF$_3$)COOCH$_3$ (161 g). Boiling point, 97°–98° C./5 mmHg.

B) The methyl ester prepared in the above step A was charged in a one liter flask and saponified with a 5% solution of sodium hydroxide in methanol at a temperature of from 40° to 60° C. in the presence of phenolphthalein as a OH indicator. From a slightly pink colored viscous solution, methanol was evaporated off under reduced pressure and the residue was dried under reduced pressure to a constant weight at 120° C. to obtain a solid product (162 g).

C) The solid product prepared in the above step B was ground and charged in a 500 ml flask connected with a trap cooled by dry ice, and the interior atmosphere of the flask was thoroughly replaced with nitrogen. Then, the flask was heated from 150° C. to 240° C. over 4 hours. A liquid material (134 g) was trapped. The trapped liquid material was distilled to recover the entitled compound (69 g). Boiling point, 70°–71° C./6 mmHg.

EXAMPLE 2

In the same manner as in Example 1 but using a perfluoropolyether mixture of CF$_3$CF$_2$CF$_2$—(OCF$_2$CF$_2$CF$_2$)$_2$—OCF$_2$CF$_2$—CF$_2$COF (91% by mole) and CF$_3$CF$_2$CF$_2$—(OCF$_2$CF$_2$CF$_2$)$_2$—OCF$_2$CF$_3$ (9% by mole) (632 g), the reaction was carried out to obtain CF$_3$CF$_2$CF$_2$—(OCF$_2$CF$_2$CF$_2$)$_3$—OCF=CF$_2$ (240 g).

EXAMPLE 3

In a 3 liter reaction vessel, pure water (1 liter), C$_3$F$_7$OCF(CF$_3$)CF$_2$OCF(CF$_3$)COONH$_4$ (100 g) as an emulsifier, disodium hydrogenphosphate dodecahydrate (10.0 g) and a perfluorovinyl ether of the formula: CF$_3$CF$_2$CF$_2$(OCF$_2$CF$_2$—CF$_2$—CF$_2$)$_3$OCF=CF$_2$ (32.0 g) were charged. After thoroughly replacing the interior atmosphere with nitrogen and evacuating the interior atmosphere to reduced pressure, hexafluoropropylene (hereinafter referred to as "HFP") was injected at 15° C. To increase the internal pressure to 0 kg/cm$^2$G and thereafter vinylidene fluoride (hereinafter referred to as "VdF") was injected to increase the internal pressure to 7 kg/cm$^2$G.

Then, a solution of sodium sulfite (13 mg) in pure water (3 ml) and a solution of ammonium persulfate (10 mg) in pure water (2 ml) were successively added together with VdF to initiate polymerization.

As the polymerization proceeded, the internal pressure dropped. When the pressure reached 6.5 kg/cm$^2$G, a monomer mixture of HFP and VdF in a molar ratio of 94:6 was injected to pressurize to 7.0 kg/cm$^2$G. While repeating pressure drop and pressurization, the perfluorovinyl ether (each 9.0 g) was added after 1.2, 2.5, 3.6 and 4.6 hours from the initiation of polymerization to continue polymerization. After 5.5 hours from the initiation of polymerization, the unreacted monomers were purged to obtain an aqueous emulsion, which was coagulated by freezing. The coagulated material was washed with water and dried under reduced pressure to obtain a rubbery copolymer (86.0 g).

$^{19}$F-NMR analysis of the copolymer revealed that the molar ratio of VdF:HFP:CF$_3$CF$_2$CF$_2$(OCF$_2$CF$_2$CF$_2$)$_3$OCF=CF$_2$ in the copolymer was 76.6:10.1:13.3. A glass transition temperature of the copolymer measured by a differential scanning calorimeter (DSC) at a temperature rising rate of 10° C./min. was −65° C. (a center value of the peak), which indicates that the copolymer has good low temperature properties.

In the subsequent Examples, the molar ratio of the monomers and the glass transition temperature were measured in the same manners as above.

EXAMPLE 4

In the same manner as in Example 3 but injecting tetrafluoroethylene (hereinafter referred to as "TFE") in place of HFP to internal pressure of 0 kg/cm$^2$G, adding a monomer mixture of VdF/TFE in a molar ratio of 92:8 to compensate the pressure drop, and adding the same perfluorovinyl ether (each 8 g) after 0.8, 1.1, 1.3 and 1.5 hours from the initiation of polymerization, the polymerization was carried out. After 1.7 hours from the initiation polymerization, the unreacted monomers were purged. In the same manner as in Example 3, the obtained aqueous emulsion was coagulated, and the coagulated material was washed with water and dried under reduced pressure to obtain a rubbery copolymer (95.6 g) having a molar ratio of VdF:TFE:CF$_3$CF$_2$—CF$_2$—CF$_2$(OCF$_2$CF$_2$CF$_2$)$_3$OCF=CF$_2$ of 72.5:13.1:14.4 and a glass transition temperature of −68° C.

EXAMPLE 5

In a 300 ml reaction vessel, pure water (100 ml), C$_3$F$_7$OCF(CF$_3$)CF$_2$OCF(CF$_3$)COONH$_4$ (10 g) as an emulsifier, disodium hydrogenphosphate dodecahydrate (1 g) and a perfluorovinyl ether of the formula: CF$_3$CF$_2$CF$_2$(OCF$_2$CF$_2$CF$_2$)$_3$O—CF=CF$_2$ (5 g) were charged. After thoroughly replacing the interior atmosphere with nitrogen and evacuating the interior atmosphere to reduced pressure, HFP was injected at 15° C. to increase the internal pressure to 0 kg/cm$^2$G and thereafter VdF was injected to increase the internal pressure to 7 kg/cm$^2$G.

Then, a solution of sodium sulfite (2.65 mg) in pure water (2.65 ml) and a solution of ammonium persulfate (1 mg) in pure water (1 ml) were successively added together with VdF to initiate polymerization.

As the polymerization proceeded, the internal pressure dropped. When the pressure reached 6.5 kg/cm$^2$G, VdF was injected to pressurize to 7 kg/cm$^2$G. With repeating pressure drop and pressurization, the polymerization was carried out. After 23 minutes from the initiation of polymerization, the unreacted monomers were purged to obtain an aqueous emulsion, which was coagulated by freezing. The coagulated material was washed with water and dried under reduced pressure to obtain a rubbery copolymer (7.9 g) having a molar ratio of VdF:HFP:CF$_3$CF$_2$CF$_2$(OCF$_2$CF$_2$CF$_2$)$_3$OCF=CF$_2$ of 74.2:7.6:18.2 and a glass transition temperature of $-65.5°$C.

EXAMPLE 6

In the same manner as in Example 5 but charging 10 g of the same perfluorovinyl ether as used in Example 5 and purging the unreacted monomer after 44 minutes from the initiation of polymerization, the polymerization was carried out to obtain an aqueous emulsion, which was coagulated by freezing. The coagulated material was washed with water and dried under reduced pressure to obtain a rubbery copolymer (9.6 g) having a molar ratio of VdF:HFP:CF$_3$CF$_2$CF$_2$(OCF$_2$CF$_2$—CF$_2$)$_3$OCF=CF$_2$ of 72.0:7.7:20.3 and a glass transition temperature of $-70°$ C.

EXAMPLE 7

In a pressure resistant 100 ml glass ampoule equipped with a valve, CF$_3$CF$_2$CF$_2$(OCF$_2$CF$_2$CF$_2$)$_3$OCF=CF$_2$ (3.0 g), 1,1,2-trichloro-1,2,2-trifluoroethane (hereinafter referred to as "R-113") (10 ml) and a solution of 2,4,5-trichloroperfluorohexanoyl peroxide in R-113 (concentration, 0.438 g/ml) (0.5 ml) were charged and cooled with dry ice/methanol followed by replacement of the interior atmosphere with nitrogen. Then, VdF (1.2 g) was charged and reacted at 20±1° C. for 30 minutes with shaking. As the reaction proceeded, the internal pressure dropped from 2.5 kg/cm$^2$G to 1.5 kg/cm$^2$G. The unreacted monomers were purged and the content in the ampoule was poured in pure water to precipitate a product, which was dried under reduced pressure to a constant weight to obtain a copolymer (2.0 g) having a molar ratio of VdF:CF$_3$CF$_2$CF$_2$(OCF$_2$CF$_2$CF$_2$)$_3$OCF=CF$_2$ of 77.0:23.0 and a glass transition temperature of $-76°$ C.

EXAMPLE 8

In the same manner as in Example 7 but charging 0.5 g of ethylene in place of VdF and proceeding the polymerization for 1 hour and 40 minutes, the polymerization was carried out. The internal pressure dropped from 1.5 kg/cm$^2$G to 1.1 kg/cm$^2$G. After drying under reduced pressure, 1.5 g of a copolymer was obtained.

$^1$H-NMR and $^{19}$F-NMR analyses of the copolymer revealed that the molar ratio of ethylene:CF$_3$CF$_2$CF$_2$(OCF$_2$CF$_2$—CF$_2$)$_3$OCF=CF$_2$ in the copolymer was 62.6:37.4. The copolymer had a glass transition temperature of $-88°$ C.

COMPARATIVE EXAMPLE 1

In the same manner as in Example 3 but initially charging perfluorovinyl ether of the formula: CF$_3$CF$_2$CF$_2$[OC—(CF$_3$)FCF$_2$]$_3$OCF=CF$_2$ (hereinafter referred to as "PB$_3$VE") (39.4 g) which is derived from hexafluoropropyleneoxide and r subsequently adding PB3VE (each 22.5 g) after 2.8, 4.5, 6.7, 7.3 and 8.2 hours from the initiation of polymerization, the polymerization was carried out. After 9.3 hours from the initiation of polymerization, the unreacted monomers were purged to obtain an aqueous emulsion, which was coagulated by freezing. The coagulated material was washed with water and dried under reduced pressure to obtain a rubbery copolymer (233 g) having a molar ratio of VdF:HFP:PB3VE of 75.7: 8.3:16.0 and a glass transition temperature of $-38.5°$ C.

COMPARATIVE EXAMPLE 2

In a 3 liter reaction vessel, pure water (1 liter) and ammonium perfluorooctanoate (2 g) as an emulsifier were charged. After thoroughly replacing the interior atmosphere with nitrogen, HFP was injected at 80° C. to increase the internal pressure to 1 kg/cm$^2$G and thereafter a monomer mixture of VdF and HFP in a molar ratio of 78:22 was injected to increase the internal pressure to 10 kg/cm$^2$G with keeping the temperature at 80° C.

Then, a solution of ammonium persulfate (2.2 mg) in pure water (50 ml) was added under pressure to initiate polymerization.

As the polymerization proceeded, the internal pressure dropped. When the pressure reached 9 kg/cm$^2$G, the same monomer mixture as above was injected to pressurize to 10 kg/cm$^2$G. The polymerization was carried out with repeating pressure drop and pressurization. After 2.3 hours from the initiation of polymerization, the unreacted monomers were purged and the reaction vessel was cooled to obtain an aqueous emulsion containing 24.3 % of solid materials. The emulsion was coagulated by adding an aqueous solution of potassium alum. The coagulated material was washed with water and dried to obtain a rubbery copolymer (331 g) having a molar ratio of VdF:HFP of 78.5:21.5 and a glass transition temperature of $-23°$ C.

The compositions, yields and glass transition temperatures of the copolymers produced in Examples 3 to 8 and Comparative Examples 1 and 2 are summarized in the following Table.

TABLE

| Example No. | Composition (% by mole) | | | | | | Yield of copolymer (g) | Tg (°C.) |
|---|---|---|---|---|---|---|---|---|
| | Ethylene | TFE | VdF | HFP | PL$_3$VE*$^1$ | PB$_3$VE | | |
| 3 | — | — | 76.6 | 10.1 | 13.3 | — | 86.0 | $-65$ |
| 4 | — | 13.1 | 72.5 | — | 14.4 | — | 95.6 | $-68$ |
| 5 | — | — | 74.2 | 7.6 | 18.2 | — | 7.9 | $-65.5$ |
| 6 | — | — | 72.0 | 7.7 | 20.3 | — | 9.6 | $-70$ |
| 7 | — | — | 77.0 | — | 23.0 | — | 2.0 | $-76$ |
| 8 | 62.6 | — | — | — | 37.4 | — | 1.5 | $-88$ |
| Comp. 1 | — | — | 75.7 | 8.3 | — | 16.0 | 233 | $-38.5$ |

TABLE-continued

| Example No. | Composition (% by mole) | | | | | | Yield of copolymer (g) | Tg (°C.) |
|---|---|---|---|---|---|---|---|---|
| | Ethylene | TFE | VdF | HFP | PL3VE*[1] | PB3VE | | |
| Comp. 2 | — | — | 78.5 | 21.5 | — | — | | −23.0 |

Note:
*[1] $CF_3CF_2CF_2(OCF_2CF_2CF_2)_3OCF=CF_2$
*[2] Melting point

EXAMPLE 9

In the same manner as in Example 7 but charging 3.6 g of TFE in place of VdF and proceeding the polymerization for 3 minutes, the polymerization was carried out. The internal pressure dropped from 4.50 kg/cm$^2$G to 4.00 kg/cm$^2$G. After drying under reduced pressure, 2.2 g of a copolymer was obtained. The copolymer had a molar ratio of TFE:$CF_3$—$CF_2CF_2(OCF_2CF_2CF_2)_3OCF=CF_2$ of 97.8:2.2.

The copolymer had a melting point (first run melting point) of 322° C., and after once melt, it had a melting point (second rum melting point) of 317° C. These melting points were measured as follows:

The powdery copolymer (3 mg) is precisely weighed and charged in a highly sensitive differentional scanning calorimeter (910 Differential Scanning Calorimeter manufactured by DuPont), and a melting point of crystalline copolymer is measured. During the measurement, an endothermic peak due to melting was recorded on a chart in proportion to an amount of heat of fusion. The powdery copolymer is heated from 250° C. to 380° C. at a raising rate of 10° C./min. The melting peak temperature recorded in this heating step is recorded as the first run melting point. Then, the copolymer is cooled to 250° C. at a cooling rate of 10° C./min. and again heated to 380° C. at a rate of 10° C./min. The melting peak temperature in the second heating step is recorded as the second run melting temperature.

EXAMPLE 10

In a stainless steel made 3 liter autoclave equipped with a temperature regulating jacket, an agitator and baffles, deionized deoxygenated water (1.45 liter), ammonium tertiary phosphate (3 mg) and ammonium perfluorooctanoate (9 mg) were charged. The interior atmosphere was evacuated, filled with nitrogen and reevacuated (these steps being repeated three times) followed by evacuation and filling with TFE twice. After final evacuation, $F(CF_2CF_2CF_2O)_4$—$CF=CF_2$ (2.2 g) was charged, and the temperature of the content was raised to 70° C. while stirring at 400 rpm.

Thereafter, TFE was injected to pressurize to 7.5 kg/cm$^2$G, and a solution of ammonium persulfate (4.0 mg) in water (50 ml) was added together with TFE to pressurize to 8.0 kg/cm$^2$G.

After several minutes, the internal pressure dropped, which indicated the initiation of polymerization. From this time, TFE was continuously injected to keep the pressure at 8.0 kg/cm$^2$G. When the total amount of the monomers (=polymer yield) reached 250 g, TFE was purged.

The powdery product was recovered from the autoclave and mixed with water and ground by a technical mixer for 1 minute. After replacing water, the powdery product was ground for additional 5 minutes. The obtained finely ground powder was dried in an air circulation type drier at 150° C. for 14 hours. The first melting point, 343.9° C.; the second melting point, 323.8° C.

Creep of an article molded from this powdery copolymer was 6.4 % at 24° C. Creep was measured as follows:

The powder (190 g) was charged in a cylinder-shape mold of 50 nun in diameter and press molded under pressure of 300 kg/cm$^2$ for a detention time of 5 minutes. The molded article was removed from the mold and heated to 365° C. in an air-sintering furnace at a rate of 50° C./hr., kept at 365° C. for 5 hours and then cooled to room temperature at a rate of 50° C./hr. The sintered article was cut to form a cylinder of 11.3 mm in diameter and 10 nun in height with coinciding the pressing direction with the cylinder height. In a thermostatic chamber kept at 24° C., a load of 140 kg/cm$^2$ was applied to the cylindrical sample. After 10 seconds and 24 hours from the start of loading, the height of the cylinder was measured. Creep was calculated from the heights after 10 seconds and 24 hours according to the following equation:

$$\text{Creep } (\%) = \frac{\text{Height after 10 sec.} - \text{Height after 24 hrs.}}{\text{Height before loading}} \times 100$$

COMPARATIVE EXAMPLE 3

In the same manner as in Example 9 but using no $F(CF_2CF_2CF_2O)_4CF=CF_2$, a polymer was prepared. Creep of an molded article from this polymer was 8.6 % at 24° C. The first run melting point, 343.9° C. The second run melting point, 326.6° C.

What is claimed is:

1. A fluorovinyl ether of the formula:

$$R_f\text{—}(OCF_2CF_2CF_2)_n\text{—}OCF=CF_2 \qquad (I)$$

wherein $R_f$ is $C_1$-$C_5$ perfluoroalkyl group, n is an integer of 2 to 4.

2. The fluorovinyl ether according to claim 1, which is $CF_3CF_2CF_2(OCF_2CF_2CF_2)_3OCF=CF_2$.

* * * * *